United States Patent
Feth et al.

(10) Patent No.: US 10,583,531 B2
(45) Date of Patent: Mar. 10, 2020

(54) METHOD FOR PRODUCING A BODY IMPLANT, ASSEMBLY CONSISTING OF A GUIDE WIRE AND A BODY IMPLANT, AND A MEDICAL INSTRUMENT

(71) Applicant: Admedes Schuessler GmbH, Pforzheim (DE)

(72) Inventors: Nils-Agne Feth, Waldbronn (DE); Alexander Lange, Karlsruhe (DE); Ralf Steiner, Pforzheim (DE)

(73) Assignee: Admedes Schuessler GmbH, Pforzheim (DE)

( * ) Notice: Subject to any disclaimer, the term of this patent is extended or adjusted under 35 U.S.C. 154(b) by 348 days.

(21) Appl. No.: 15/450,994

(22) Filed: Mar. 6, 2017

(65) Prior Publication Data
US 2017/0173738 A1  Jun. 22, 2017

Related U.S. Application Data

(62) Division of application No. 14/404,336, filed as application No. PCT/EP2013/000185 on Jan. 22, 2013, now Pat. No. 10,434,605.

(30) Foreign Application Priority Data

May 30, 2012 (DE) .......................... 10 2012 010 687

(51) Int. Cl.
*B23K 26/364* (2014.01)
*A61F 2/01* (2006.01)
(Continued)

(52) U.S. Cl.
CPC .......... *B23K 26/364* (2015.10); *A61B 17/221* (2013.01); *A61F 2/01* (2013.01);
(Continued)

(58) Field of Classification Search
CPC .............. B23K 26/364; B23K 26/0624; B23K 2101/32; A61F 2/89; A61F 2/91;
(Continued)

(56) References Cited

U.S. PATENT DOCUMENTS 5,376,100 A   12/1994  Lefebvre et al.
5,495,668 A   3/1996   Furusawa et al.
(Continued)

FOREIGN PATENT DOCUMENTS

DE   197 22 429 A1   12/1998
DE   197 45 294 A1   4/1999

OTHER PUBLICATIONS

International Search Report and Written Opinion for PCT/EP2013/000185, dated Apr. 4, 2013, 10 pages.
(Continued)

*Primary Examiner* — John C Hong
(74) *Attorney, Agent, or Firm* — Harrity & Harrity, LLP (57) ABSTRACT

The invention relates to a method for producing a body implant comprising the steps of: providing a wire; producing predetermined cuts of the cross section of the wire by means of an ultrashort pulse laser in order to produce a predetermined shape of the body implant. This method can be used to produce, for example, a body implant, an assembly consisting of a guide wire and a body implant, or a medical instrument having a guide wire.

18 Claims, 8 Drawing Sheets

(51) Int. Cl.
  *A61F 2/89* (2013.01)
  *A61B 17/221* (2006.01)
  *B23K 26/0622* (2014.01)
  *A61F 2/91* (2013.01)
  *B23K 101/32* (2006.01)
  *A61B 17/00* (2006.01)

(52) U.S. Cl.
  CPC .......... *A61F 2/89* (2013.01); *A61F 2/91* (2013.01); *B23K 26/0624* (2015.10); *A61B 2017/00526* (2013.01); *A61B 2017/00867* (2013.01); *A61B 2017/2212* (2013.01); *A61F 2002/018* (2013.01); *A61F 2210/0014* (2013.01); *A61F 2230/005* (2013.01); *A61F 2230/0097* (2013.01); *A61F 2240/001* (2013.01); *B23K 2101/32* (2018.08)

(58) Field of Classification Search
  CPC .......... A61F 2/01; A61F 2230/005; A61F 2230/0097; A61F 2002/018; A61F 2210/0014; A61F 2240/001; A61B 17/221; A61B 2017/00867; A61B 2017/2212; A61B 2017/00526
  See application file for complete search history.

(56) References Cited

U.S. PATENT DOCUMENTS

| | | |
|---|---|---|
| 5,573,520 A | 11/1996 | Schwartz et al. |
| 5,707,387 A | 1/1998 | Wijay et al. |
| 5,916,235 A | 6/1999 | Guglielmi |
| 5,980,514 A | 11/1999 | Kupiecki et al. |
| 6,022,369 A | 2/2000 | Jacobsen et al. |
| 6,160,240 A | 12/2000 | Momma et al. |
| 6,190,402 B1 | 2/2001 | Horton et al. |
| 6,258,117 B1 | 7/2001 | Camrud et al. |
| 6,299,612 B1 | 10/2001 | Ouchi et al. |
| 6,398,791 B1 | 6/2002 | Que et al. |
| 6,402,771 B1 | 6/2002 | Palmer et al. |
| 6,551,342 B1 | 4/2003 | Shen et al. |
| 6,579,246 B2 | 6/2003 | Jacobsen et al. |
| 6,893,450 B2 | 5/2005 | Foster et al. |
| 7,060,083 B2 | 6/2006 | Gerberding et al. |
| 7,377,925 B2 | 5/2008 | Poll et al. |
| 7,524,322 B2 | 4/2009 | Monstadt et al. |
| 7,632,242 B2 | 12/2009 | Griffin et al. |
| 7,771,410 B2 | 8/2010 | Venturelli et al. |
| 7,828,832 B2 | 11/2010 | Belluche et al. |
| 7,850,708 B2 | 12/2010 | Pal et al. |
| 7,857,008 B2 | 12/2010 | Chen et al. |
| 7,914,466 B2 | 3/2011 | Davis et al. |
| 7,914,467 B2 | 3/2011 | Layman et al. |
| 8,016,870 B2 | 9/2011 | Chew et al. |
| 8,251,963 B2 | 8/2012 | Chin et al. |
| 8,292,827 B2 | 10/2012 | Musbach et al. |
| 8,323,241 B2 | 12/2012 | Salahieh et al. |
| 8,409,114 B2 | 4/2013 | Parins et al. |
| 8,523,879 B1 | 9/2013 | Lind et al. |
| 8,529,596 B2 | 9/2013 | Grandfield et al. |
| 8,708,953 B2 | 4/2014 | Salahieh et al. |
| 8,795,254 B2 | 8/2014 | Layman et al. |
| 8,821,477 B2 | 9/2014 | Northrop et al. |
| 8,876,772 B2 | 11/2014 | Weber et al. |
| 8,961,550 B2 | 2/2015 | Lenker et al. |
| 9,011,480 B2 | 4/2015 | Divino et al. |
| 9,067,332 B2 | 6/2015 | Lippert et al. |
| 9,067,333 B2 | 6/2015 | Lippert et al. |
| 9,072,874 B2 | 7/2015 | Northrop et al. |
| 9,144,665 B2 | 9/2015 | Salstrom et al. |
| 9,149,609 B2 | 10/2015 | Ansel et al. |
| 9,717,612 B2 | 8/2017 | Dorn et al. |
| 9,795,307 B2 | 10/2017 | Radman et al. |
| 9,795,765 B2 | 10/2017 | Romoscanu et al. |
| 2001/0041899 A1 | 11/2001 | Foster |
| 2002/0010481 A1 | 1/2002 | Jayaraman et al. |
| 2002/0065553 A1 | 5/2002 | Weber |
| 2004/0138677 A1 | 7/2004 | Little et al. |
| 2005/0182390 A1 | 8/2005 | Shanley et al. |
| 2007/0010762 A1 | 1/2007 | Ressemann et al. |
| 2007/0043413 A1 | 2/2007 | Eversull et al. |
| 2007/0067019 A1 | 3/2007 | Miller et al. |
| 2007/0112373 A1 | 5/2007 | Carr, Jr. et al. |
| 2007/0142901 A1 | 6/2007 | Steinke et al. |
| 2007/0225729 A1 | 9/2007 | Cheng et al. |
| 2008/0039930 A1 | 2/2008 | Jones et al. |
| 2008/0208211 A1 | 8/2008 | Uihlein et al. |
| 2008/0312597 A1 | 12/2008 | Uihlein et al. |
| 2009/0088832 A1 | 4/2009 | Chew et al. |
| 2009/0248133 A1 | 10/2009 | Bloom et al. |
| 2010/0102046 A1 | 4/2010 | Huang et al. |
| 2010/0168758 A1 | 7/2010 | Uihlein et al. |
| 2010/0318115 A1 | 12/2010 | Chanduszko et al. |
| 2011/0009950 A1 | 1/2011 | Grandfield et al. |
| 2011/0070358 A1 | 3/2011 | Mauch et al. |
| 2011/0160838 A1 | 6/2011 | Blanzy et al. |
| 2011/0245907 A1 | 10/2011 | Pacetti et al. |
| 2011/0288630 A1 | 11/2011 | Blanzy et al. |
| 2011/0319988 A1 | 12/2011 | Schankereli et al. |
| 2012/0046687 A1 | 2/2012 | Trommeter et al. |
| 2013/0289701 A1 | 10/2013 | Coghlan et al. |
| 2015/0165558 A1 | 6/2015 | Feth et al. |
| 2018/0008439 A9* | 1/2018 | Tieu .................. A61F 2/852 |

OTHER PUBLICATIONS

Official Communication for corresponding EP Application No. 13 703 522.6-1651, dated Apr. 22, 2014, 5 pages.
International Preliminary Report on patentability for PCT/EP2013/000185, dated Dec. 11, 2014, 6 pages.

* cited by examiner

METHOD FOR PRODUCING A BODY IMPLANT, ASSEMBLY CONSISTING OF A GUIDE WIRE AND A BODY IMPLANT, AND A MEDICAL INSTRUMENT

RELATED APPLICATIONS

This application is a divisional of U.S. patent application Ser. No. 14/404,336, filed Dec. 10, 2014, which claims priority to PCT Application No. PCT/EP2013/000185, filed Jan. 22, 2013, which claims priority to German Application No. 10 2012 010 687.4, filed May 30, 2012, the contents of which are incorporated herein by reference.

The present invention relates to a method for producing a body implant, an assembly consisting of a guide wire and a body implant, and a medical instrument.

Conventionally, body implants and medical instruments, such as stents, baskets, filters or catching devices are made of hollow round material, like e.g. a tube. Alternatively or additionally, such devices may be produced by braiding wires. This measure, however, involves high production expenditure, and devices produced in this way have a limited crimp capability, i.e. a capability of reducing their diameter for insertion into the human body. Thus, there is need for a method and for devices produced by this method, having a higher crimp capability and a simpler production method.

Thus, the object of the invention is to provide a simplified method and corresponding devices which simplify the production of stents, baskets, filters and the like, and which allow for higher crimp capability.

This object is accomplished by the features of the independent claims. Advantageous embodiments of the invention are defined in the dependent claims.

According to one aspect, the invention relates to a method for producing a body implant, comprising the steps of:
providing a wire,
producing cuts, or notches, or structures, respectively, on the wire's cross section using an ultrashort pulse laser, in order to produce a predetermined shape of the body implant.

Preferably, the cuts are produced substantially in radial direction, and a cut portion of the wire, or a wire segment, is expanded in order to produce a body implant, such as a closed basket or a filter, stent or the like.

A part, preferably the major part of the wire's cross section can be removed by the cuts, for example, in order to produce a joint.

Still preferentially, the method can further include the step of braiding wire segments and/or a step of shaping wire segments.

Preferably, a wire is used which is made of a material having shape-memory properties, such as Nitinol.

The ultrashort pulse laser technology allows for micro treatment of materials, such as wires without having to expel the removed material, such as re-solidified mass in the case of conventional laser fusion cutting. Hence, a process of cold removal, a so-called ablation process, takes place. In contrast to conventional laser fusion cutting where only continuous cuts can be made, there is the possibility of structuring a wire, on the one hand, thus altering the mechanical and/or electrical or electronic properties. On the other hand, this process allows for slitting very fine wires symmetrically as well as asymmetrically by cuts. Thus, by producing radial cuts in the wire, wire segments can be separated from the wire, and subsequently can be shaped and/or expanded in order to produce a basket, a stent, or a filter, for example. Moreover, the wire segments can be braided in order to systematically manipulate mechanical and electrical or electronic properties.

Moreover, the cuts or notches or structures, respectively, can be produced such that an integrally formed joint is produced from the wire by means of removing a major part of the cross section. Thus, numerous configurations are possible by means of generating corresponding cuts on a wire using the ultrashort pulse laser technology.

According to a further aspect, the invention relates to an assembly consisting of a guide wire and a body implant produced by means of such a method, with the guide wire and the body implant being integrally, or monolithically, formed and having a predetermined breaking point. Herein, the guide wire can have at least an integrally formed joint in order to increase the flexibility or bending property of the guide wire.

Preferably, the assembly has at least one of a stent, a basket or a filter.

According to a further aspect, a medical instrument having a guide wire is provided that is produced using this method. Therein, the guide wire can have at least an integrally formed joint.

The advantage of this manufacturing technology is that an assembly consisting of a guide wire and a body implant, or a medical instrument, respectively, can be made of one piece, such that connecting a guide wire with a body implant by means of micro welding, for example, is no longer necessary. Thus, a fault susceptibility of a corresponding assembly consisting of a guide wire and a medical instrument is considerably reduced.

This integrally formed assembly can have a predetermined breaking point such that the body implant, or the medical instrument, is separated from the guide wire after positioning in the human body in order to remove the guide wire. Further, the production process is highly simplified. Moreover, the guide wire can have an integrally formed joint in order to provide higher flexibility.

This technology has the advantage of having lower raw material costs, is mechanically stronger and has maximal crimp capability, since the expanded wire segments can be deformed or crimped so as to assume the original position of the uncut wire, in order to reduce the diameter for insertion into the human body to a minimal diameter. Moreover, the device can be produced with a minimal number of production steps.

The invention will now be explained in more detail based on exemplary embodiments with reference to the accompanying drawings.

Figure 1:
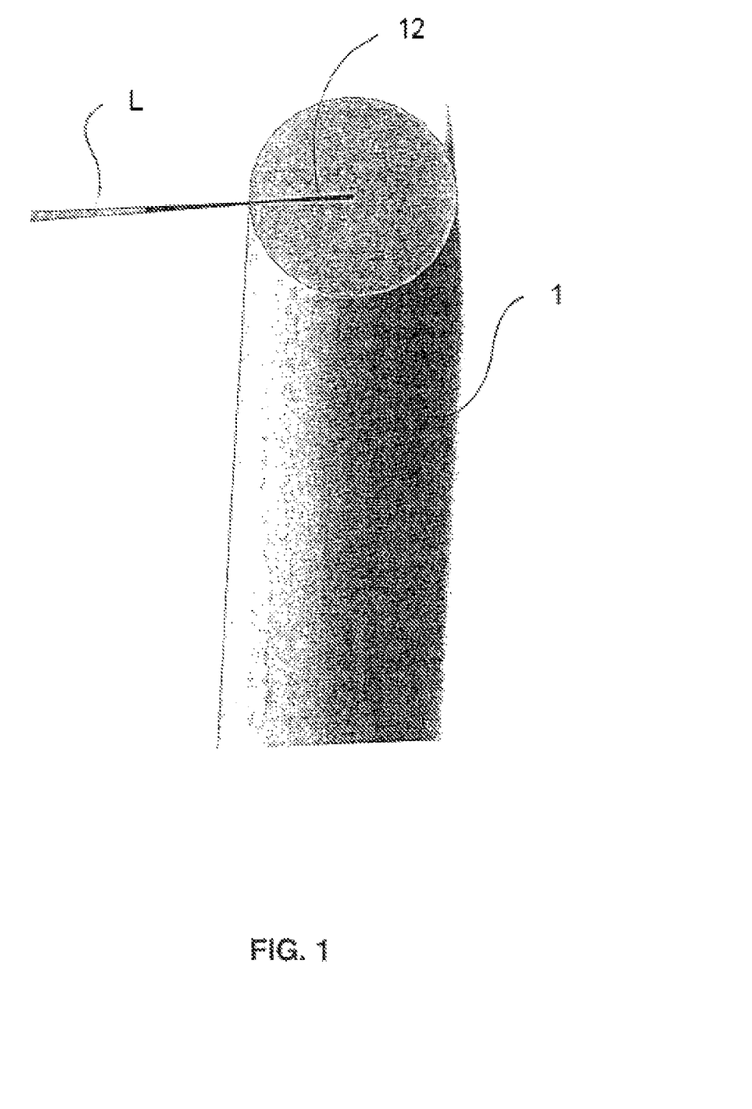
FIG. 1 shows a circular wire being cut by a laser beam in radial direction approximately up to its center.

As shown in FIG. 1, a circular wire 1 is cut in up to approximately the center thereof by means of a laser beam L using the ultrashort pulse laser technology, in order to generate a cut 12. Although circular wires are advantageously used for this technology, the invention is not restricted thereto. Wires having elliptical cross sections, triangular, square, pentagon wires, or the like can also be used.

Advantageously, an ultrashort pulse laser having a wavelength of about 200 to about 2000 nm is used therein. The pulse width should be about 10 fs to about 10 ps.

Figure 2:
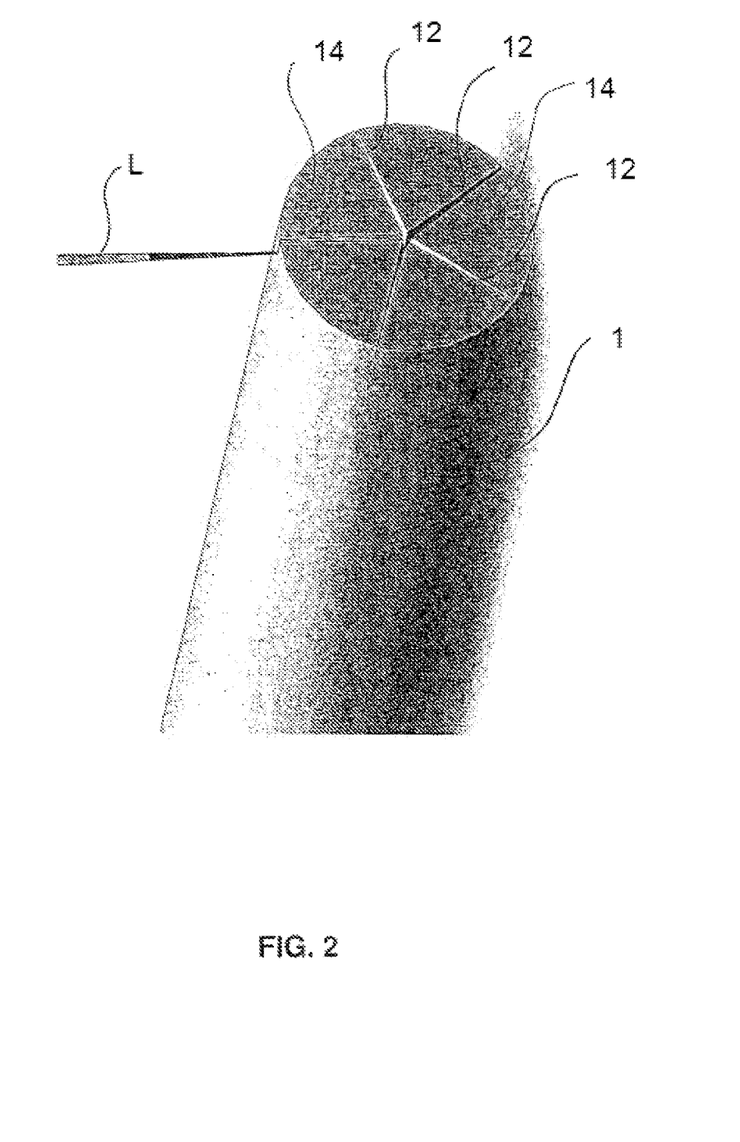
FIG. 2 shows the production of five cuts in total in a radial direction up to the wire's center.

Further, for example, five radial cuts extending to the center of the wire can be generated, in order to produce wire segments or cut sectors 14, as shown in FIG. 2. These cut sectors or wire segments 14 subsequently can be expanded by deformation so as to produce, for example, a basket or filter design, as shown for example in FIG. 3. Therein, the cuts do not extend up to an axial end 1a, 1b of the wire 1, such that the individual wire segments 14 remain connected in longitudinal directions at their ends.

Figure 3:
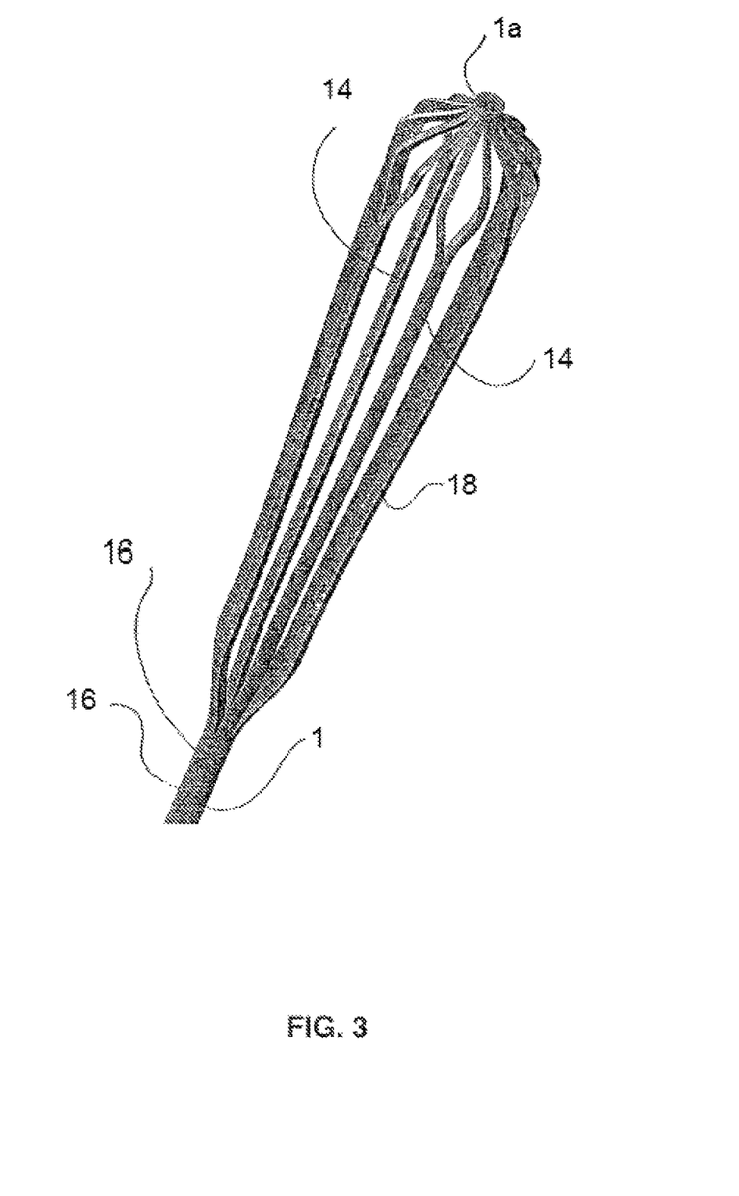
FIG. 3 shows a design of a basket or filter produced by the cuts wherein the cut wire segments are subsequently expended.

In this manner, a basket or filter design, respectively, is produced having wire segments 14 which are integrally connected at their ends 1a, 1b.

This means that the wire 1 is divided, like a pie, into individual segments (wire segments 14), wherein axial ends 1a, 1b of the wire are not separated. The separated wire segments 14 are expanded such that a body is generated having spaced wire segments 14 in the axial center and axial ends 1a, 1b which are integrally connected to the wire segments 14.

It should be appreciated that the invention can also be realized with three, four, six or seven cuts 12, etc. Therein, the cuts 12 do not have to be set at regular angular distances, but "pieces of pie", or wire segments 14, of different sizes can be generated.

Figure 8A:
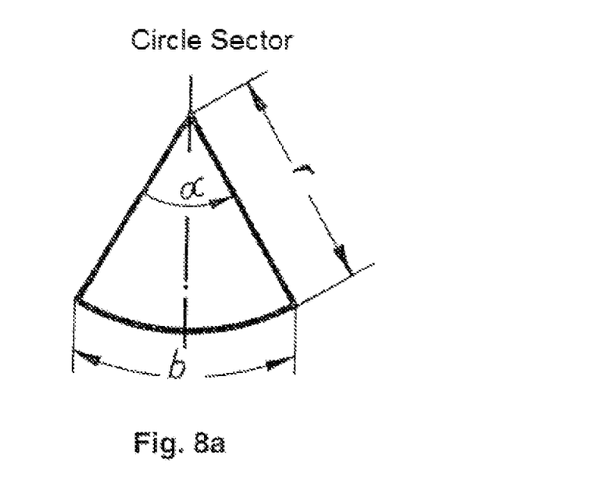
FIG. 8a shows a wire segment formed as a circle sector.
Figure 8B:
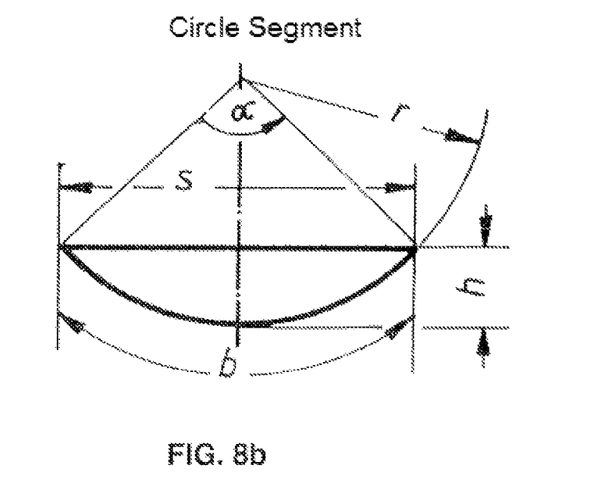
FIG. 8b shows a wire segment formed as a circle segment.

Moreover, the wire segments 14 do not have to be generated as a circle sector having the length of the radius r of the wire 1 as sides of the circle sector, i.e. by means of cuts 12 ending at the center of the wire cross-section, as shown in FIG. 8a, but any forms can be separated from the wire cross-section, such as a circle segment, as shown for example in FIG. 8b.

A circle segment, as shown in FIG. 8b, is separated from the wire cross-section by producing a cut 12 offset from the center of the wire cross-section along the chord length s. Therein, a height h of the cut 12 is smaller than the radius r of the wire.

By means of separating wire segments 14 with different cross sections from the wire cross-section in this manner, and expanding them subsequently, a stent can be generated, for example, having varying supporting powers along the circumference thereof.

These wire segments 14 can be deformed or treated according to the desired mechanical and/or electrical properties by further shaping by means of forming or by further laser treatment. Moreover, the wire segments 14 can be braided, e.g. by tatting the wire segments with the weave types 1/2, 1/1, or 2/2.

The basket or filter design, or stent 18, respectively, produced this way can subsequently be separated from the wire 1. It can, however, also remain connected to a longer piece of wire 1 such that the uncut end of the wire 1 is used as a guide wire 16, as shown for example in FIGS. 4 and 5.

Figure 4:
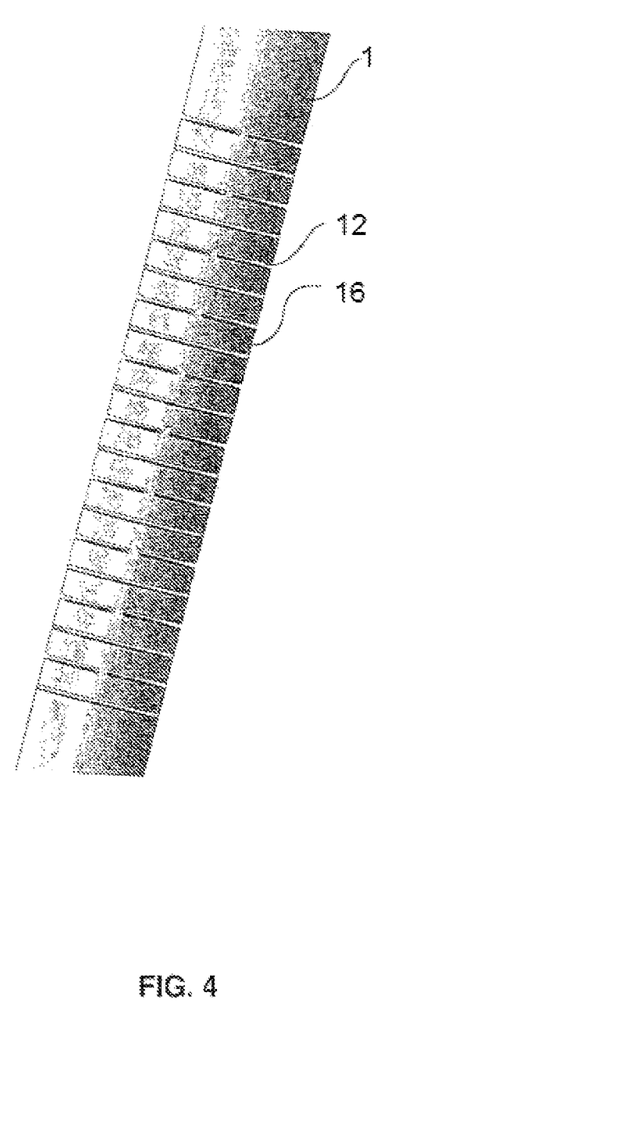
FIG. 4 shows a guide wire exhibiting high bending property or flexibility due to the generation of corresponding cuts.
Figure 5:
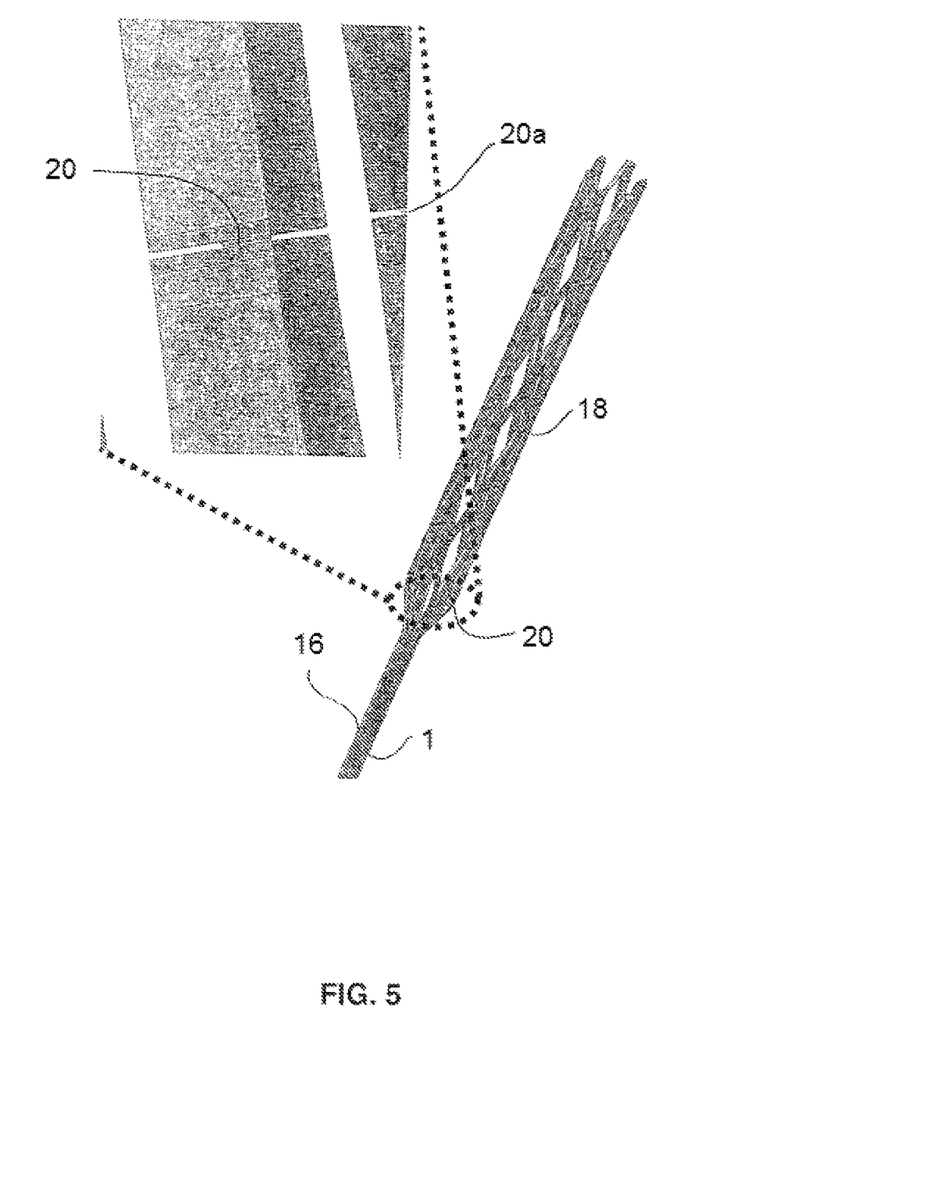
FIG. 5 shows a stent integrally formed with the guide wire and having a predetermined breaking point.

A predetermined breaking point 20 can be provided between the guide wire 16 and the body implant 18 generated, such that the assembly consisting of the guide wire 16 and the body implant 18, which is integrally formed in this manner, can be separated at the predetermined breaking point 20 after insertion and positioning of the body implant 18, in order to remove the guide wire 16 after positioning of the body implant 18. Therein, the guide wire 16 can have corresponding cuts 12 or sectional weakenings or structures, respectively, in order to provide for high flexibility or bending property. The predetermined breaking point 20 has a corresponding sectional weakening 20a, in order to facilitate breaking or separating at the predetermined breaking point 20.

Figure 6:
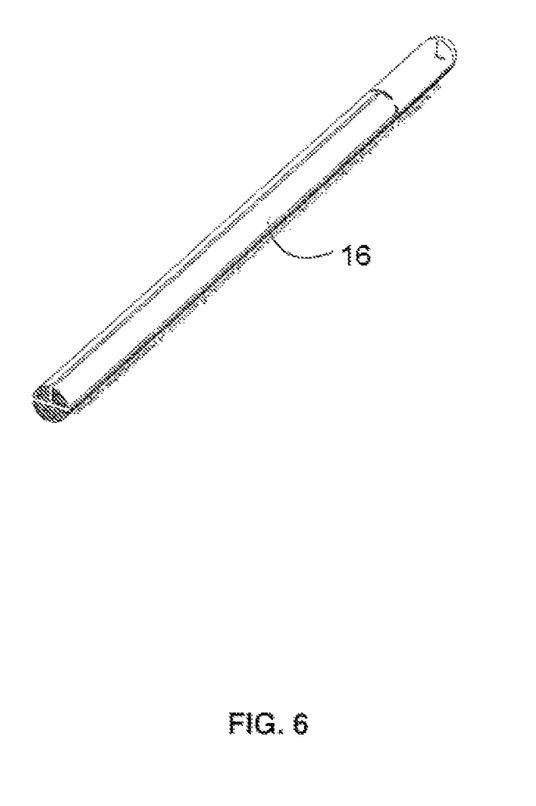
FIG. 6 shows a controllable guide wire.
Figure 7:
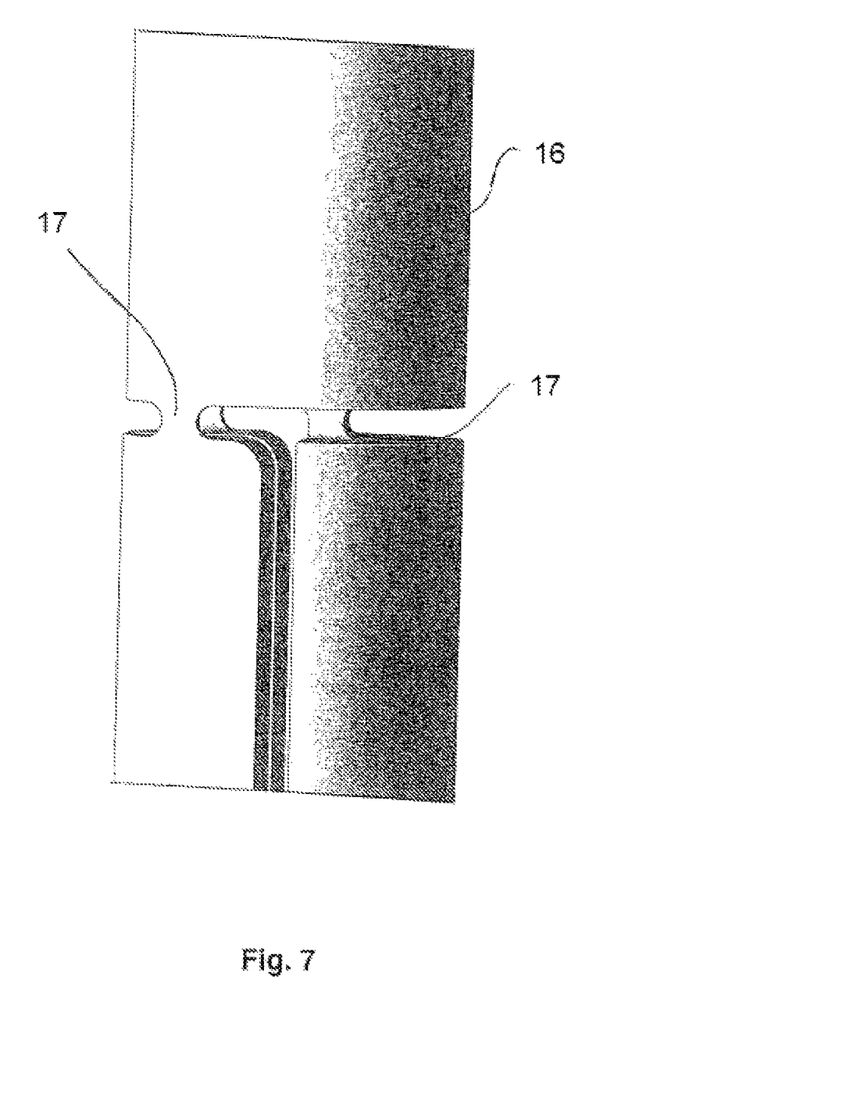
FIG. 7 shows a detailed view of the guide wire of FIG. 6 with a corresponding joint for bending the guide wire.

As further shown in FIGS. 6 and 7, a corresponding joint 17 can be produced by a cut wherein almost the whole cross section of the wire or guide wire 16, respectively, is removed, around which joint one end of the guide wire 16 can be bent with respect to another segment.

Thus a variety of design possibilities is provided by correspondingly cutting a wire 1 using the ultrashort pulse laser technology, and by expanding and, if applicable, further treating the cut wire segments 14. Thus, a body implant 18, e.g. a stent, a basket, or a filter can be produced as one piece in a simple manner. Moreover, this body implant 18 can be crimped to the original wire diameter in order to achieve maximal reduction of diameter.

Preferably, a wire 1 is used which is made of a material having shape-memory properties, such as Nitinol. However, other metals or nonmetals can also be employed.

The invention is not limited to the production of radial cuts 12, but cuts can be made also in other directions. Moreover, the cuts 12 do not have to reach the center of the wire 1, but depending on the application can be produced with less or more depth.

Structures or notches on the cross section of the wire 1 can be generated thereby.

LIST OF REFERENCE SIGNS 1 wire
12 cut
14 wire segment
16 guide wire
17 joint
18 body implant (stent)
20 predetermined breaking point
20a sectional weakening
L laser

The invention claimed is:

1. A method comprising:
    providing a wire;
    producing cuts on the wire by means of an ultrashort pulse laser in order to produce a shape of a body implant; and
    producing one or more other cuts on the wire in a manner that provides a predetermined breaking point between a guide wire, formed from the wire, and the body implant, wherein the cuts do not extend up to a first axial end or a second axial end of the wire.

2. The method according to claim 1,
    wherein the cuts are produced substantially in radial direction,
    wherein a cut segment of the wire or a wire segment is expanded in order to produce the body implant, and
    wherein the body implant is a closed basket or a filter.

3. The method according to claim 1, wherein a portion of cross section of the wire is removed in order to produce a joint.

4. The method according to claim 1, further comprising:
    braiding or tatting wire segments and/or shaping wire segments.

5. The method according to claim 1, wherein the wire is made of a material having shape-memory properties.

6. The method according to claim 1, wherein the predetermined breaking point is configured for the body implant to be separated from the guide wire after positioning of the body implant in a body.

7. The method according to claim 1, further comprising:
separating wire segments, with different cross-sections, from the wire.

8. The method according to claim 7, wherein the body implant has varying supporting powers along a circumference of the body implant due to the wire segments being separated.

9. The method according to claim 1, wherein the wire is made of a material having shape-memory properties.

10. The method according to claim 1, wherein the cuts extend to a center of the wire.

11. The method according to claim 1, wherein a height of a cut, of the cuts, is smaller than a radius of the wire.

12. A method comprising:
providing a wire;
dividing the wire into individual wire segments in order to produce a shape of a body implant; and
producing one or more other cuts on the wire in a manner that provides a predetermined breaking point between a guide wire, formed from the wire, and the body implant.

13. The method according to claim 12, further comprising:
expanding the wire segments into the shape of the body implant.

14. The method according to claim 12, wherein the wire segments are integrally connected to at least one of a first axial end or a second axial end of the wire.

15. The method according to claim 14, wherein the first axial end and the second axial end are not separated after the cuts.

16. A method comprising:
providing a wire;
producing cuts on the wire in order to produce a shape of a body implant; and
crimping the body implant to an original diameter of the wire.

17. The method according to claim 16, wherein the cuts do not extend up to a first axial end or a second axial end of the wire.

18. The method of claim 16, wherein a cut segment of the wire or a wire segment is expanded in order to produce the body implant.

* * * * *